US005997895A

United States Patent [19]

Narotam et al.

[11] Patent Number: 5,997,895
[45] Date of Patent: Dec. 7, 1999

[54] DURAL/MENINGEAL REPAIR PRODUCT USING COLLAGEN MATRIX

[75] Inventors: Pradeep K. Narotam, Winnipeg, Canada; James R. van Dellen, Glenwood, South Africa; Robert P. O'Fee, West Chester, Pa.; George W. McKinney, III, Chestnut Hill, Mass.; Simon J. Archibald, Pennington; Judith O'Grady, Marlboro, both of N.J.

[73] Assignee: Integra Lifesciences Corporation, Plainsboro, N.J.

[21] Appl. No.: 09/070,659

[22] Filed: Apr. 30, 1998

Related U.S. Application Data

[60] Provisional application No. 60/059,089, Sep. 16, 1997, and provisional application No. 60/064,261, Nov. 4, 1997.

[51] Int. Cl.⁶ ........................................................ A61F 2/00
[52] U.S. Cl. .............................................. 424/423; 602/50
[58] Field of Search ................................ 424/423; 602/50

[56] References Cited

U.S. PATENT DOCUMENTS

| | | | |
|---|---|---|---|
| 3,157,524 | 11/1964 | Artandi | 106/122 |
| 3,520,402 | 7/1970 | Nichols et al. | 206/63.3 |
| 4,016,877 | 4/1977 | Cruz, Jr. et al. | 602/50 |
| 4,066,083 | 1/1978 | Ries | 424/400 |
| 4,578,067 | 3/1986 | Cruz, Jr. | 602/50 |
| 5,019,087 | 5/1991 | Nichols | 606/657 |
| 5,667,839 | 9/1997 | Berg | 426/657 |

OTHER PUBLICATIONS

Adegbite, A. B.; Paine, K. W.; Rozdilsky, B. The role of neomembranes in formation of hematoma around Silastic dura substitue. Case report. J. Neurosurg. 1983 Feb; 58(2): 295–7.

Anonymous. Creutzfeldt–Jakob disease in patients who received a cadaveric dura mater graft—Spain, 1985–1992. MMWR Morb Mortal Wkly Rep. Jul. 23, 1993; 42(28):560–3.

Anonymous. Leads from the MMWR. Update: Creutzfeldt–Jakob disease in a patient receiving a cadaveric dura mater graft. JAMA. Jul. 17, 1987; 258(3): 309–10.

Anonymous. Leads from the MMWR. Creutzfeldt–Jakob disease in a second patient who received a cadaveric dura mater graft. JAMA. Feb. 24, 1989; 261(8): 1118.

Anonymous. Update: Creutzfeldt–Jakob disease in a patient receiving a cadaveric dura mater graft. MMWR. Morb Mortal Wkly Rep. Jun. 5, 1987; 36(21):324–5.

Anonymous. Update: Creutzfeldt–Jakob disease in a second patient who received a cadaveric dura mater graft. MMWR Morb. Mortal Wkly Rep. Jan. 27, 1989; 38(3):37–8, 43.

Antoine, J. C.; Michel D.; Bertholon, P.; Mosnier, J. F.; Laplanche, J. L.; Beaudry, P.; Hauw, J. J.; Veyret, C. Creutzfeldt–Jakob disease after extracranial dura mater embolization for a nasopharyngeal angiofibroma. Neurology. 1997 May; 48(5):1451–3.

Awwad, E. E.; Smith, K. R. Jr; Martin, D. S.; Manealli, A. Unususal hemorrhage with use of synthetic dural substitute: MR findins. J. Comput Assist Tomogr. 1991 Jul.; 15(4):618–20.

Banerjee, T.; Meagher, J. N.; Hunt, W. E. Unusual complications with use of silastic dural substitute. Am. Surg. 1974 Jul; 40(7):434–7.

Berrington, N. R. Acuten extradural hematoma associated with silastic dural substitute: case report. Surg Neurol. 1992 Dec; 38(6):469–70.

Brown, P.; Cervenakova, L.; Goldfarb, L. G.; McCombie, W. R.; Rubenstein, R.; Will, R. G.; Pocchiari, M.; Martinez–Lage, J. F.; Scalici, C.; Masullo, C.; et al. Iatrogenic Creutzfeldt–Jakob disease: an example of the interplay between ancient genes and modern medicine. Neurology. 1994 Feb; 44(2):291–3.

Clavel, M.; Clavel, P. Creutzfeldt–Jakob disease transmitted by dura mater graft. Eur Neurol. 1996; 36(4):239–40.

Cohen, A. R.; Aleksic, S.; Ransohoff, J. Inflammatory reaction to synthetic dural substitute. Case report. J. Neurosurg. 1989 Apr; 70(4):633–5.

Defebvre, L.; Destee, A.; Caron, J.; Ruchoux, M. M.; Wurtz, A.; Remy, J. Creutzfeldt–Jakob disease after an embolization of intercostal arteries with cadaveric dura mater suggesting a systemic transmission of the piron agent. Neurology. 1997 May; 48(5):1470–1.

Esmode, T.; Lucek, C. J.; Symon, L.; Duchen, L. W.; Will, R. G. Creutzfeldt–Jakob disease and lyophilised dura mater grafts: report of two cases. J. Neurol Neurosurg Psychiatry. 1993 Sep; 56(9):999–1000.

Fisher, W. S. 3d; Six, E.G. Cervical myelopathy from dural substitute. Neurosurgery. 1983 Dec; 13(6):715–7.

Fontana, R.; Talamonti, G.; D'Angelo, V.; Arena, O.; Monte, V.; Colice, M. Spontaneous haematoma as unusual complication of silastic dural substitute. Report of 2 cases. Acta Neurochir. 115(1–2(Wien) 1992):64–6.

Gondo, G. et al. A Posterior fossa hemorrhage 11 years after the use of silastic dural substitute: case report. [Japanese with English abstract]. No Shinkei Geka. 1991. Jan; 19(1):59–62.

Gudmundsson, G.; Sogaard, I. Complications to the use of vicryl–collagen dural substitute. Acta Neurochir. 132(1–3 (Wien) 1995): 145–7.

(List continued on next page.)

*Primary Examiner*—Jon P. Weber
*Attorney, Agent, or Firm*—Caesar, Rivise, Bernstein, Cohen & Pokotilow, Ltd.

[57] ABSTRACT

Dural substitutes are provided, which include collagen treated and/or prepared to be physiologically compatible and substantially free of active viruses and prions. Suitable forms for the dural substitutes include a sponge, a film, a non-woven matrix, a felt or a combination of at least two of the foregoing forms. Also provided are a method for preparing dural substitutes and a method for promoting meningeal tissue growth.

78 Claims, No Drawings

OTHER PUBLICATIONS

Hainfellner, J. A.; Jellinger, K.; Dringer, H.; Guentchev, M.; Kleinert, R.; Pilz, P.; Maier, H.; Budka, H. Creutzfeldt–Jakob disease in Austria. [German with English abstract]. Wien Klin Wochenschr. Dec. 13, 1996; 108(23): 759–63.

Harvey, I.; Coyle, E. Creutzfeldt–Jakob disease after non–cmmercial dura mater graft. Lancet. Sep. 5, 1992; 340(8819):615.

Janetta et al., "Formaldehyde–treated, regenerated collagen film and film–laminate as a substitute for dura mater." 16 Surg. Forum 435 (1965).

Johnson, M. H.; Thompson, E. J. Freeze–dried cadaveric dural grafts can stimulate a damaging immune response in the host. Eur. Neurol. 1981; 20(6):445–7.

Lane, K. L.; Brown, P.; Howeel, D. N.; Crain, B. J.; Hulette, C. M.; Burger, P. C.; DeArmond, S. J. Creutzfeldt–Jakob disease in a preganat woman with an implanted dura mater graft. Neurosurgery. 1994 Apr;34(4):737–9; discussion 739–40.

Laquerriere, Annie M.D., et al. "Experimental evaluation of bilayered human collagen as a dural substitute" J Neurosurg 1993 78:487–491.

Martinez–lage, J. F.; Sola, J.; Poza, M.; Esteban, J. A. Pediatric Creutzfeldt–Jakob disease: probable transmission by a dural graft. Childs Nerv Syst. 1993 Jul; 9(4):239–42.

Marx, R. E.; Carlson, E. R. Creutzfeldt–Jakob disease from allogenic dura: a review of risks and safety. J. Oral Maxillofac Surg. 1991 Mar.; 49(3):272–274; discussion 274–275.

Misra, B. K.; Shaw, J. F. Extracrebral hematoma in association with dural substitute. Neurosurgery. 1987 Sep; 21(3):399–400.

Miyamoto, S. et al. "Formation of postoperative hematoma directly under a silastic dural substitute." [Japanese with English Abstract.] No Shinkei Geka. 1983 Sep; 11(9)989–994.

Newcombe, R. L. Neurosurgery and iatrogenic transmission of Creutzfeldt–Jakob disease. Med J Aust. May 20, 1996; 164(10):603–4.

Ng, T. H.; Chan, K. H.; Leung, S. Y.; Mann, K. S. An unusual complication of silastic dural substitute: case report. Neurosurgery. 1990 Sep;27(3):491–3.

Ohbayashi, N.; Inagawa, T.; Katoh, Y.; Kumano, K.; Nagasakio, R.; Hada, H. Complication of silastic dural substitute 20 years after dural plasty. Surg Neurol. 1994 Apr;41(4):338–41.

Ongkiko, C. M. Jr; Keller, J. T.; Mayfield, F. H.; Dunsker, S. B. An unusual complication of Dura Film as a dural substitute. Report of two cases. J. Neurosurg. 1984 May;60(5):1076–9.

Pocchiari, M.; Masullo, C.; Salvatore, M.; Genuardi, M.; Galgani, S. Creutzfeldt–Jakob disease after non–commerical dura mater graft. Lancet. Sep. 5, 1992; 340(8819):614–5.

Robertson, S. C.; Menezes, A. H. Hemorrhagic complications in association with silastic dural substitute: pediatric and adult case reports with a review of the literature. Neurosurgery. 1997 Jan;40(1):201–5; discussion 205–6.

Santos, Garcia, J. M.; Lopez Corbalan, J. A.; Martinez–Lage, J. F.; Sicilia Guillen, J. CT and MRI in iatrogenic and sporadic Creutzfeldt–Jakob disease: as far as imaging perceives. Neuroradiology. 1996 Apr; 38(3):226–31.

Siccardi, D.; Ventimigilia, A. Fibrotic–haemorrhagic reaction to synthetic dural substitute. Acta Neurochir. 132(1–3(Wien) 1995): 148–9.

Simpson, D.; Robson, A. Recurrent Subarachnoid bleeding in association with dural substitute. Report of three cases. J Neurosurg. 1984 Feb;60(2):408–9.

Thadani, V.; Penar, P. L.; Partington, J.; Kalb, R.; Janssen, R.; Schonberger, L. B.; Rabkin, C. S.; Prichard, J. W. Creutzfeldt–Jakob disease probably acquired a cadaveric dura mater graft. Case report. J Neurosurg. 1988 Nov;69(5):766–9.

Taylor, D. M.; McConnell, I. Unconventional transmissible agents in dura mater: significance for iatrogenic Creutzfeldt–Jakob disease. Neuropathol Appl Neurobiol. 1996 Jun;22(3): 259–60.

Thompson, D.; Taylor, W.; Hayward, R. Haemorrhage associated with silastic dural substitute. J Neurol Neuorsurg Psychiatry. 1994 May;57(5):646–8.

Weber, T.; Tumani, H.; Holdorff, B.; Collinge, J.; Palmer M.; Kretzschmar, H. A.; Felgenhauer, K. Transmission of Creutzfeldt–Jakob disease by handling of dura mater. Lnacet. Jan. 9, 1993;341(8837):123–4.

Yamada, S.; Aiba, T.; Endo, Y.; Hara, M.; Kitamoto, T.; Tateishi, J. Creutzfeldt–Jakob disease transmitted by a cadaveric dura mater graft. Neurosurgery. 1994 Apr;34(4):740–3; discussion 743–4.

Xu Bang–Zong et al., "Study and clinical application of a porcine biomembrane for the repair of dural defects" J Neurosurg. 1988 69:707–711.

Kline, David G. MD et al. "Dural Replacement With Resorbable Collagen" Arch Surg. 1965 Dec. 91:924–929.

Fletcher, Lee J. et al. "Experimental Evaluation of Silicon–Coated Dacron and Collagen Fabric–Film Laminate as Dural Substitutes" 558–564.

Narotam, Pradeep K., "Experimental evaluation of collagen sponge as a dural graft" British Journal of Neurosurger 1993 7:635–641.

Narotam, Pradeep K., "A clinicopathological study of collagen sponge as a dural graft in neurosurgery" J Neurosurg 1995 82:406–412.

Collins, Ronald L. L. "Use of collagen film as a dural substitute: Preliminary animal studies" 1991 25:267–276.

DURAL/MENINGEAL REPAIR PRODUCT USING COLLAGEN MATRIX

CROSS-REFERENCES TO RELATED APPLICATIONS

This application claims the benefits of U.S. Provisional Application No. 60/059,089, filed Sep. 16, 1997, and U.S. Provisional Application No. 60/064,261, filed Nov. 4, 1997.

FIELD OF THE INVENTION

This invention relates to the repair of damaged tissue, and more specifically, to the use of noninfectious collagen to heal damaged dural tissue.

BACKGROUND OF THE INVENTION

The human brain and spinal cord are covered with meningeal membranes whose integrity is critical to the operation of the central nervous system. When the integrity of a person's meningeal membranes is intentionally or accidentally compromised, serious consequences may ensue, unless the membranes can be repaired.

The meningeal membrane comprises three overlapping layers of tissue, which are in order from outside to inside, the dura mater (or dura), the arachnoid and the pia mater. Repairing damaged meningeal membranes has largely focused on implantable and/or resorbable constructs (known as dural substitutes) which are grafted over the damaged dura mater and are designed to replace and/or regenerate the damaged tissue. Researchers have experimented with a wide variety of substances as dural substitutes, but have not found a dural substitute that is safe, effective and mass-marketable.

Autologous grafts of tissue from other parts of the body, such as fascia lata and pericardium, can be effective as dural substitutes; however, autologous tissue is relatively difficult to obtain and can require the additional costs and risks of a second operation for the patient. By definition, such tissues cannot be mass-marketed.

Cadaverous dura mater has also been employed as a dural substitute. Like autologous tissues, cadaverous tissues can be difficult to obtain, and thus cannot be mass-marketed. Only about 4 to 5 transplantable units can be prepared from each donor, and cultural biases make it difficult to readily obtain donors.

More importantly, cadaverous dural substitutes have been implicated in the transmission of prion infections. An Oct. 6, 1997 meeting of the U.S. Food and Drug Administration (FDA) relating to such dural substitutes resulted in a call for stricter processing controls, and a warning that such dural substitutes might be banned if adequate safety precautions are not employed to prevent transmission of infections, such as Creutzfeld-Jakob disease (CJD). Regulatory agencies in other countries, such as the Japanese Ministry of Health, have gone even further by banning the use of cadaverous dura mater in brain surgery. Moreover, the World Health Organization (WHO) has recommended banning the use of cadaverous dura mater in brain surgery because of the risk of CJD transmission.

Dural substitutes comprising gold, silver, platinum, nickel, steel or gelatin have been researched; however, they have been found unacceptable for a variety of reasons, including high rigidity, poor incorporation, fibrosis, low resistance to infection and excessive foreign body response or regenerative processes. See, e.g., the references listed in the attached Bibliography.

Numerous studies have evaluated the safety and effectiveness of xenografts using non-human tissues as dural substitutes. Although non-human tissues are more readily harvested and mass-marketed than human tissues, they have not performed ideally as human dural substitutes.

Intact bovine pericardium tissue implants, while perhaps the most popular dural substitute in the U.S. at present, may transmit bovine spongiform encephalopathy (BSE). Intact tissues can cause excessive fibrosis and encapsulation, possibly resulting in the development of hemorrhagic complications, such as the formation of subdural hematomas and even death. Xenografting with porcine biomembrane has been shown to result in severe adhesions when infection occurred in animal studies, and xenografting with certain collagen laminates or collagen films has been shown to result in a severe inflammatory response comprising fibrosis, neomembrane formation and meningeocerebral adhesions. See Bang-Zong et al., "Study and clinical application of a porcine biomembrane for the repair of dural defects," 69 J. Neurosurg. 707 (1988); Kline, "Dural replacement with resorbable collagen," 91 Arch. Surg. 924 (1965); Jannetta et al., "Formaldehyde-treated, regenerated collagen film and film-laminate as a substitute for dura mater," 16 Surg. Forum 435 (1965); and Lee et al., "Experimental evaluation of silicone-coated Dacron and collagen fabric-film laminate as dural substitutes," 27 Neurosurg. 558 (1967).

A physiologically compatible dural substitute that does not create adhesions is particularly important when there is a need for repeated surgical treatment. In treating brain cancer, for example, cancers can recur, requiring repeated opening and closing of the dura mater to gain access to the recurring cancer and/or even repeated removal of cancerous sections of the dura mater. Patient outcomes could be improved by repairing the damaged dural tissue with a physiologically compatible dural substitute that does not create life-threatening adhesions. Moreover, doctors would be more willing to surgically intervene where indicated if the likelihood of creating adhesions were reduced.

Despite the previously reported problems with collagen xenografts, the inventors continued to work with collagen as a dural substitute. In 1993 and 1995, Narotam et al. (groups including some of the present inventors) reported that a collagen sponge showed promise as a dural substitute. See Narotam et al., "Experimental evaluation of collage sponge as a dural graft," 7 British J. Neurosurg. 635 (1993), and Narotam et al., "A clinicopathological study of collagen sponge as a dural graft in neurosurgery," 82 J. Neurosurg. 406 (1995). Although the collagen sponge disclosed in these papers appeared to effectively function as a dural substitute, there were significant safety issues still to be recognized and resolved.

The collagen sponge used (i.e., Bicol®) was bovine in origin and, despite its prior use as a temporary protective material on the brain surface beneath retractors, the collagen was not sufficiently decontaminated so as to preclude the possibility of causing a xenogenic infection when permanently implanted. Contrary to the knowledge and teachings of the 1995 article at page 410, right column, it is now known that the collagen sponge disclosed in the Narotam et al. articles poses a health hazard due to the possibility of infectious agents (e.g., prions and viruses) surviving the manufacturing process. The lack of significant chemical processing does not provide a suitable safety margin for the inactivation of viral or prion contaminants and therefore cannot adequately prevent, or reduce the likelihood of, infecting dural substitute recipients.

Thus, there has been a need for a mass-marketable collagen-based dural substitute that would be physiologically compatible (i.e., non-inflammatory, non-adhesion inducing, etc.), sufficiently noninfectious (i.e., decontaminated, etc.) to prevent the transmission of viruses and prions to dural substitute recipients, pliable, available in a variety of sizes, high in tensile strength, inert, optionally capable of forming a water-tight seal, and optionally suturable.

All references cited herein, including prior patent applications, are incorporated herein by reference in their entireties.

SUMMARY OF THE INVENTION

The instant invention addresses at least the foregoing deficiencies of the prior art in providing a meningeal tissue growth matrix produced by a method comprising preparing physiologically compatible collagen which is substantially free of active viruses and prions, and forming a porous meningeal tissue growth matrix therewith.

The invention also provides a method for promoting meningeal tissue growth, said method comprising preparing physiologically compatible collagen which is substantially free of active viruses and prions, forming a matrix with said collagen, and contacting said matrix and damaged meningeal tissue to promote meningeal tissue growth.

The invention further provides a method for preparing a meningeal tissue growth matrix, said method comprising preparing physiologically compatible collagen which is substantially free of active viruses and prions, providing a volume of said collagen in a liquid medium and evaporating said liquid medium to provide the meningeal tissue growth matrix.

DETAILED DESCRIPTION OF PREFERRED EMBODIMENTS

The inventors have discovered that collagen processed using an alkaline/salt treatment in accordance with U.S. Pat. No. 5,019,087, is an extremely effective dural replacement product that will lead to the regeneration of a patient's own functional dura. The preferred alkaline/salt treatment involves sodium hydroxide and sodium sulfate. The methods of U.S. Pat. No. 5,019,087 provide a controlled predictable pore size.

Further, the method for producing the product of the present invention makes use of steps that are recognized as the most effective for inactivating viral and prion contamination. This gives the product a very high safety level while eliminating the inflammatory response. That is, the method for producing the product of the invention provides a product that is substantially free of viruses and prions without being physiologically incompatible. The phrase "substantially free of viruses and prions" means that the product does not contain infection-effective amounts of viruses and prions. More specifically, the invention preferably comprises the use of collagen treated by a process sufficient to achieve at least a 4 log clearance of virus, more preferably at least a 6 log clearance of virus, and even more preferably at least an 8 log clearance of virus, as measured with a statistical confidence level of at least 95%. For example, if the concentration of virus before treatment is $10^7$ and after treatment is $10^1$, then there has been an 6 log clearance of virus.

In preparing the dural substitutes of the present invention, a collagen dispersion is first prepared in a manner well known in the art. One such preparation is taught in U.S. Pat. No. 3,157,524. Another suitable preparation of collagen is taught in U.S. Pat. No. 3,520,402.

In particular, the collagen dispersions of the present invention may be prepared by the following methods.

A native source of Type I collagen, such as skin, tendons, ligaments or bone, is first mechanically or hand cleaned of fat, fascia and other extraneous matter and washed. The cleaned and washed collagen containing material is then comminuted, generally by slicing or grinding.

The material is then subjected to an enzyme treatment while under intermittent stirring with a proteolytic enzyme, such as ficin, pepsin, and the like, so as to remove non-collagenous impurities which may cause antigenic activity and to swell the collagen by removing elastin. The amount of enzyme added to the collagen material and the conditions under which enzyme digestion takes place is dependent upon the particular enzyme being used. Generally, when using ficin, which is most commonly used, the pH is adjusted to about 6.0 to 6.3, and the collagen material is digested for about 1 to 2 hours at a temperature of about 36.5° C. to 37.5° C. with one part ficin for every 150 parts of collagen material. After the requisite amount of time, the enzyme is inactivated by appropriate means well known in the art, such as by the addition of a solution of an oxidizing agent, such as sodium chlorite when the enzyme is ficin.

The enzyme treated collagen containing material is then washed to remove excess enzyme and the non-collagenous protein impurities. Preferably, the washing is carried out with ultrafiltered and deionized water and optionally further washed with dilute aqueous hydrogen peroxide.

In a preferred embodiment of the present invention, the enzyme digested collagen containing material is then further subjected to an alkali treatment at a pH of about 13 to 14, at a temperature of about 25° C. to 30° C. for a period of about 35 to 48 hours, preferably about 40 hours. Suitably, the alkali treatment is carried out in an aqueous solution of 5% sodium hydroxide and 20% sodium sulfate. This alkali treatment removes contaminating glycoproteins and lipids. The solution is then neutralized with a suitable acid, such as aqueous sulfuric acid, and thoroughly washed.

The collagen material is then further swollen with a suitable acid solution which acid does not cause any cross-linking of the collagen. Such acids are well known to those skilled in the art and include acetic acid, hydrochloric acid, lactic acid, and the like. Regardless of which acid is used, the pH of the acid collagen dispersion is in the range of about 2 to 3.

The dispersed collagen mixture is then homogenized by any conventional means, such as a blender or homogenizer, so as to further dissociate the fibers and then filtered to remove unswollen, non-collagenous material by means well known in the art, such as by passing the dispersion through a 100 mesh stainless steel screen. The resulting filtered collagen dispersion can then be used to prepare the dural substitute products of the present invention.

Alternatively, physiologically compatible collagen which is substantially free of active viruses and prions can be obtained from transgenic animals bred for the purpose of synthesizing human collagen in a readily harvestible form. See, e.g., U.S. Pat. No. 5,667,839 to Berg. Since transgenic animals can be bred and maintained in controlled environments, which prevent them from carrying infections which must be inactivated, the collagen harvested therefrom is physiologically compatible and substantially free of active viruses and prions without further treatment (although further treatment can be performed for an added measure of safety).

The product of the present invention is preferably a matrix provided in the form of a collagen sponge. The product can also be provided in the form of a non-woven matrix, felt or film. In addition, the product can be provided in the form of a composite of any two or more of the foregoing forms, such as, e.g., a film/sponge or a film/sponge/film.

A collagen sponge according to the invention can be provided by adaptation of the methods for forming collagen sponges disclosed in U.S. Pat. No. 5,019,087. The sponge can be prepared by lyophilization of a collagen dispersion prepared according to the patent, preferably having a concentration of between 0.1 and 10% solids (w:w) and more preferably at least 0.75% solids. A volume of the dispersion is poured into a suitable (preferably non-stick) tray to provide a sponge having a suitable shape. Preferably, the sponge has a thickness from about 2.5 mm to about 5 mm, and more preferably 3 mm. The dispersion is then frozen and lyophilized for about 1 to about 48 hours, with the most preferable cycle being that described in U.S. Pat. No. 5,019,087.

The density of the dispersion and the lyophilization cycle dictate the sponge density and pore size. The sponge density is preferably about 0.0001 mg/mm$^3$ to about 0.12 mg/mm$^3$, more preferably about 0.009 mg/mm$^3$.

Sponges of the invention preferably have pores of a sufficient size and quantity to permit growing meningeal tissue to infiltrate therein. The pore size preferably ranges from about 10 $\mu$m to about 500 $\mu$m, more preferably from about 50 $\mu$m to about 150 $\mu$m, with surface pores being smaller than cross-sectional (internal) pores. In particularly preferred embodiments, the surface pores range in diameter from about 30 $\mu$m to about 150 $\mu$m, with about 70 $\mu$m being most preferred, and the cross-sectional pores range in diameter from about 50 $\mu$m to about 300 $\mu$m, with about 150 $\mu$m being most preferred.

A film according to the invention can be provided by casting a dispersion of collagen having a collagen concentration of about 0.1 to about 10% solids (w:v) and, optionally, about 0.005 to 0.5% (w:w on collagen solids) of a suitable biocompatible plasticizer, such as glycerine. Preferably, the plasticizer concentration is about 0.1% and the collagen concentration is about 1%, more preferably 0.75%. A volume of the dispersion is poured into a suitable non-stick container and evaporated to provide a film having a thickness of about 0.05 to about 2.0 mm, preferably about 0.5 mm. The film can be cross-linked with heat or a suitable chemical cross-linking agent. See, e.g., *Chemistry of Protein Conjugation and Crosslinking*, (Wong, ed., CRC Press, 1993).

As with the sponge, felt and non-woven embodiments of the invention, films of the invention preferably have pores of a sufficient size and quantity to permit growing meningeal tissue to infiltrate therein.

A non-woven matrix according to the invention is a random distribution of collagen fibers derived from collagen dispersions prepared as described above. Collagen-based non-woven matrixes are disclosed, for example, in U.S. Pat. Nos. 4,578,067 and 4,016,877.

Collagen-based felts are disclosed, for example, in U.S. Pat. No. 4,066,083.

The product can also be provided in the form of a combination of any two or more of the foregoing forms. In such an embodiment, all of the forms need not be sufficiently porous to promote tissue growth therethrough, as long as at least one sufficiently porous form is accessible to the growing tissue.

It is particularly preferred to provide the product of the invention in the form of a laminate of a collagen sponge and a collagen film. This laminate, which can be formed, e.g., by laminating a collagen sponge to a collagen film with a biocompatible adhesive or polymer (including collagen), by forming a sponge on a film, or by forming a film on a sponge, possesses the elevated water impermeability and suturability of a film, and the elevated porosity of a sponge, which facilitates dural tissue growth therethrough. Similarly, a sandwich-type laminate can be provided by providing a collagen sponge between opposing sheets of collagen film.

In certain embodiments, the film can have a shape that perfectly mirrors the underlying surface of the sponge to which it is bonded. In other embodiments, the bonding surface of the sponge does not identically correspond in shape and/or size to the bonding surface of the film. For example, a film can be sandwiched between two opposing sponges which do not overhang the ends of the film (thus leaving the edges of the film uncovered), or a film can be sandwiched between two opposing sponges which overhang the ends of the film and are bonded together as well as to the intermediate film (thus completely encasing the film in the sponges).

Laminates of film and sponge are particularly suitable for use as dura substitutes for the skull base, as they are better adapted to withstand the elevated hydraulic pressure to which dural defects in the skull base area are subjected.

It is particularly preferred to prepare sponge/film laminates by casting a collagen film; drying the film; casting a collagen slurry onto the dried film; lyophilizing the slurry/film combination; and cross-linking the lyophilized laminate product by exposing it to vapors from an aqueous formaldehyde solution (preferably having a 9.6% formaldehyde concentration) for about ninety minutes at about 25° C., followed by forced air ventilation for about one hour.

The collagen film and slurry are preferably cast from lactic acid derived collagen fibers. Such fibers are produced by a process comprising dispersing a virus and prion free collagen source (e.g., alkali-treated bovine tendon slices) in an aqueous solution of lactic acid (preferably about 85%), homogenizing the dispersion, filtering the homogenized lactic acid dispersion, and precipitating collagen fibers from the homogenized lactic acid dispersion by addition of aqueous ammonium hydroxide (preferably 0.35%) sufficient to adjust the pH to about 4.6–4.9.

Lactic acid derived/ammonium hydroxide precipitated collagen fibers are much longer than fibers produced by mechanical/chemical disruption of raw bovine tendon material. During ammonium hydroxide precipitation, the collagen fibers re-coil and are therefore longer. Longer fibers provide greater strength to the final product. The enhanced strength of products of the invention produced according to this particularly preferred method can be sufficiently strong to be watertight and suturable without the need for cross-linking, thus allowing the degree of cross-linking to be selected based on the desired rate of bioresorption.

The product can include biocompatible and/or bioresorbable materials other than collagen, although collagen is most preferred. For example, in certain embodiments it is advantageous to laminate the collagen matrix to a non-collagen film, such as a 50:50 dl lactide:co-glycolide polymer having a molecular weight of about 75,000, more preferably about 100,000. Additional suitable polymers include, e.g., biocompatible and/or bioresorbable lactides, glycolides, and copolymers thereof, polycaprolactones, polyethylene carbonate, tyrosine polycarbonates, tyrosine polyacids, and polyanhydrides. The molecular weight of the polymer is preferably about 5000 to about 500,000.

The product preferably includes effective amounts of meningeal tissue growth factors and/or bioactive peptides, such as, e.g., RGD containing peptides, decorin, laminin, merosin, chondroitin sulfate, dermatin sulfate, heparan sulfate, keratin sulfate, basic fibroblast growth factor (bFGF), fibronectin and other integrin ligands, entactin and tenascin. In certain embodiments, an effective amount of such an additive is about 1 µg/mg collagen.

The product is preferably nonantigenic in addition to being noninfectious and physiologically compatible.

The product is suitable for repairing intentional damage to the meningeal tissues, as in surgery, and consequential damage to the meningeal tissues, as might occur as a result of accidental head trauma.

After brain surgery, the product of the present invention is inserted to occupy space left by the removal resultant on surgery. As to meningeal repair following a craniotomy or a laminectomy, particularly with the incision through the dura, the product of the present invention can simply be implanted in contact with the cranial or spinal dura defect created by the surgery. Although it can be preferred to simply contact the damaged meningeal tissue and adjacent undamaged tissue with the product (particularly when the product is being used as a cranial dura substitute), the product can also be mechanically bonded (e.g., sutured) and/or chemically bonded to the damaged tissue and adjacent undamaged tissue (e.g., fibrin glue).

The product preferably connects undamaged portions of meningeal tissue adjacent to the damaged meningeal tissue by overlapping these undamaged tissues. The damaged tissue can be, e.g., torn, cut, excised or lacerated, and can be located in, e.g., the human spinal dura or the human cerebral dura. Regenerated meningeal tissue grows within the product, while the product remains implanted within a patient. That is, the product acts as a matrix or scaffold for tissue growth, such as for reparative tissue growth.

The product is substantially resorbed within about three months after implantation.

Although the product of the invention is particularly suitable for dural repair, it is also suitable for promoting tissue growth and/or wound healing in other contexts. For example, the product is suitable for use as a bioresorbable pledget to assist in suturing, a suturable hemostatic device, hernia patches, pericardial patches, and the like.

In the product, the collagen is preferably at least about 80% pure, substantially free of all prion and viral contamination, has less than 0.03 eu/gm endotoxins, has not more than 5% fat content, has at least 10% hydroxyproline content and has not more than 5% ash content. Although it is presently preferred that the product be derived from bovine corium or bovine tendon collagen, the collagen can be obtained from other sources, including other tissues and other animals, including transgenic animals.

The invention will be illustrated in more detail with reference to the following Examples, but it should be understood that the present invention is not deemed to be limited thereto.

EXAMPLE 1

Preparation of a suturable dural regeneration matrix capable of providing a water-tight seal Alkali-treated bovine tendon slices were produced according to the method described above and in U.S. Pat. No. 5,019,087. A 1250 ml aqueous dispersion containing 0.75 wt. % of the alkali-treated bovine tendon slices was then prepared. 7.5 ml of 85% (AR grade, v/v) lactic acid were slowly added to the dispersion with continuous stirring.

The dispersion was then allowed to stand at room temperature for one hour, during which it was stirred with a steel rod for twenty seconds three times—at fifteen, thirty and forty-five minutes into the hour.

The dispersion was then homogenized using a Silverson Model L4R (Thomas Scientific, USA) operated at full-speed using 9.5 mm circles (disintegrating head) for 30 seconds, 2.25 mm circles (high shear head) for 30 seconds, and 1.5 mm circles (emulsor head) for 20 seconds.

The dispersion was then sequentially vacuum filtered through a 100 mesh stainless steel filter, and then through a 200 mesh stainless steel filter. The filtrate was degassed until no visible air bubbles were present (about 30 minutes), thus providing a lactic acid dispersion.

Collagen fibers were precipitated from the lactic acid dispersion by slowly adding 0.35% (AR grade, v/v) ammonium hydroxide to the dispersion in 0.5 to 1 ml amounts, until a final pH of about 4.6 to 4.9 was reached.

600 g of the dispersion (0.76%) was then cast into a 20 cm×10 cm steel tray and air-dried for five days at room temperature. A 0.25 mm thick film having a density of 25 mg/cm$^2$ was obtained. After rehydrating, this opaque, flexible film was able to hold 410 chronic gut suture material against a pull-out force exceeding 400 g, despite the fact that the film was not cross-linked.

EXAMPLE 2

Preparation of a suturable dural regeneration matrix capable of providing a water-tight seal A 10% solution (w/w) of a 50:50 dl lactide:co-glycolide polymer, MW=75,000, (Sigma) in ethyl acetate was prepared by weighing out 90 grams (±0.5 gram) of dry ethyl acetate (Aldrich) into a suitable glass beaker fitted with a magnetic stir bar. The beaker was then placed on top of a magnetic stirrer/hot plate and gently stirred. The temperature was raised to about 30° C.–35° C. Next, 10 grams (±0.1 gram) of the lactide:glycolide polymer were added slowly to the ethyl acetate to provide the polymer solution. The solution was then allowed to cool to room temperature.

After cooling to room temperature, 50 grams of the polymer solution were poured into a 3.5"×3.5" Teflon-coated tray. The solvent was allowed to flash-off and the resulting film allowed to dry overnight at room temperature. The remaining polymer solution was covered and stored for use in the subsequent step.

After the film had dried overnight at room temperature, it was removed from the tray and placed on a large, flat Teflon-coated tray. To the air-side surface of the cast film was applied a sufficient amount of the polymer solution to afford a tacky surface. Applying the polymer solution with a paint brush works well. Next, a 3.5"×3.5" sponge according to the invention was provided and immediately placed on the tacky surface of the polymer film. Gentle pressure was applied to insure a complete bond between the collagen sponge and the copolymer film.

After about five minutes, the laminated construction was placed into a vacuum chamber, and subjected to a vacuum of at least 50 microns for 24 hours to remove any final traces of solvent.

The resulting laminated construction is a soft pliable material that can be sutured using standard surgical techniques.

EXAMPLE 3

Preparation of a suturable, dual density dural regeneration template 10 grams of a 3% dispersion of collagen in deionized water adjusted to pH 6.5–7.5 and pretreated in such a manner so as to remove or inactivate essentially all viral and prion contamination, was poured into a 3.5"×3.5" polycarbonate tray and frozen solid in a lyophilizer with a shelf temperature of $\leq 35°$ C. Once the collagen had frozen solid, 20 grams of a second dispersion of collagen (0.8%, pH 6.5 to 7.5) was poured on top of the first dispersion and immediately placed back into the lyophilizer. After freezing the tray of collagen dispersions at −35° C. for four hours, the vacuum was turned on and the material lyophilized. The resulting sponge was dehydrothermally cross-linked at 110° C. for 48 hours at full vacuum of at least 50 microns. The cross-linked sponge had excellent physical properties and could be sutured, making it an excellent candidate for a dural graft.

EXAMPLE 4

Preparation of a dual density, laminated dural graft

The dual density matrix from Example 2 was laminated to a lactide:glycolide film as described in Example 1. The resulting matrix had excellent physical properties, could be sutured using standard surgical techniques and provided a water-tight barrier.

EXAMPLE 5

Preparation of a suturable dural regeneration matrix that provides a water-tight seal A prion and virus inactivated collagen film was cast from an aqueous dispersion (0.85% solids) which included between 0.1% and 0.2% glycerine as a plasticizer. 30 grams of the dispersion was poured into a 3.5"×3.5" tray and the water was allowed to evaporate. The resulting film was then cross-linked at 110° C. under vacuum of at least 50 microns for 48 hours. The cross-linked film was placed back into the casting tray, and deionized water was added to the tray to wet-out the film. After about 1 minute, excess water was poured off and then 30 grams of the same prion and viral inactivated collagen dispersion was poured on the top of the film. The composite was then frozen and lyophilized. The resulting sponge/film composite was then cross-linked with formaldehyde. The composite was suturable and provides a water-tight seal when implanted.

EXAMPLE 6

Preparation of a suturable dural regeneration sandwich-type matrix which provides a water-tight seal Films are prepared as described above. However, in this case, 15 grams of slurry was first poured into the 3.5"×3.5" casting tray and frozen. A film was then wet-out as described above and placed on the frozen collagen dispersion. Finally, 15 grams of the collagen dispersion was poured on top of the film and the new sandwich composite was lyophilized and cross-linked with formaldehyde.

In Examples 4 and 5, the collagen film was cross-linked with heat prior to making the composite. It is possible to use a film that is not cross-linked and use the final formaldehyde treatment to cross-link the entire composite at the end of the preparation.

Further, in all of the composite (or laminate) examples described above, the film's length and width matches exactly the length and width of the sponge. It is also possible to make a composite where the film is larger than the sponge. In the case of a film having sponges on opposing surfaces thereof, the opposing sponges can meet to form a margin which surrounds the sponge, thus providing an island-type composite.

EXAMPLE 7

Dural repair in treating brain cancer

Diagnostic imaging indicated that a forty-year-old woman, who had previously undergone surgery for carcinoma of the breast, had an enhancing lesion in the posterior fossa of the left cerebellar hemisphere and two other small deposits in the left frontal lobe. In addition, the lesion in the posterior fossa was starting to generate edema, with the potential to occlude the fourth ventricle and cause hydrocephalus and raised intra-cranial pressure.

A posterior fossa craniectomy was performed under general anesthesia to excise the cerebellar metastasis. A midline incision was made and the posterior neck muscles were then dissected off to reveal the bony suboccipital region. Dissection was carried up to C2, and the arch of C1 and the remote posterior fossa were identified. A burr hole was made in the left suboccipital region. This was followed by a craniectomy which was carried up to the region of the tonsillar sinus. The dura was then opened to reveal and excise the metastatic deposit. After inspecting the resection cavity for residual tumor, it was packed with hydrogen peroxide sponges to achieve hemostasis. The cavity was then lined with Surgicel. The dural edges were then coagulated where necessary for hemostasis and a sponge according to the invention was applied across the dural wound to promote dural repair. A Hemovac drain was installed, the muscles and skin were closed using staples, and Bacitracin ointment and Mepore dressing were applied to the wound. The patient was transferred to the Recovery Room in stable condition.

EXAMPLE 8

Dural repair in treating aneurysms

A patient presented with an aneurysmal subarachnoid hemorrhage due to a ruptured anterior communicating artery aneurysm and was treated by a pterional craniotomy. The temporalis muscle was reflected inferiorly together with the scalp flap and a free bone flap over the pterion was created using a drill. Following this, the sphenoid ridge was then leveled down to allow for greater access. Once the bony decompression was performed, the dura was cut open. The aneurysm was dissected off its adhesions and thereafter successfully clipped. The temporary clips were then removed and hemostasis was achieved. The basal cisterns were copiously irrigated. Gelfoam soaked with Papaverine was temporarily applied to the vessels and then removed. Once hemostasis was achieved, the dura was reconstructed by overlapping the damaged dura and adjacent undamaged dura with a sponge according to the invention. Following this, the bone flap was secured into position using Nylon ties. A Hemovac drain was inserted beneath the galea, and the scalp was closed in two layers and secured with clips.

The patient was thereafter transferred to the Intensive Care Unit in stable condition.

While the invention has been described in detail and with reference to specific examples thereof, it will be apparent to one skilled in the art that various changes and modifications can be made therein without departing from the spirit and scope thereof.

BIBLIOGRAPHY (PARTIAL)

1. Adegbite, A. B.; Paine, K. W.; Rozdilsky, B. The role of neomembranes in formation of hematoma around Silastic dura substitute. Case report. J Neurosurg. 1983 February; 58(2): 295–7.
2. Anonymous. Creutzfeldt-Jakob disease in patients who received a cadaveric dura mater graft—Spain, 1985–1992. MMWR Morb Mortal Wkly Rep. 1993 Jul. 23; 42(28): 560–3.
3. Anonymous. Leads from the MMWR. Update: Creutzfeldt-Jakob disease in a patient receiving a cadaveric dura mater graft. JAMA. 1987 Jul. 17; 258(3): 309–10.
4. Anonymous. Leads from the MMWR. Creutzfeldt-Jakob disease in a second patient who received a cadaveric dura mater graft. JAMA. 1989 Feb. 24; 261(8): 1118.
5. Anonymous. Update: Creutzfeldt-Jakob disease in a patient receiving a cadaveric dura mater graft. MMWR Morb Mortal Wkly Rep. 1987 Jun. 5; 36(21): 324–5.
6. Anonymous. Update: Creutzfeldt-Jakob disease in a second patient who received a cadaveric dura mater graft. MMWR Morb Mortal Wkly Rep. 1989 Jan. 27; 38(3): 37–8, 43.
7. Antoine, J. C.; Michel, D.; Bertholon, P.; Mosnier, J. F.; Laplanche, J. L.; Beaudry, P.; Hauw, J. J.; Veyret, C. Creutzfeldt-Jakob disease after extracranial dura mater embolization for a nasopharyngeal angiofibroma. Neurology. 1997 May; 48(5): 1451–3.
8. Awwad, E. E.; Smith, K. R. Jr; Martin, D. S.; Manepalli, A. Unusual hemorrhage with use of synthetic dural substitute: MR findings. J Comput Assist Tomogr. 1991 July; 15(4): 618–20.
9. Banerjee, T.; Meagher, J. N.; Hunt, W. E. Unusual complications with use of silastic dural substitute. Am Surg. 1974 July; 40(7): 434–7.
10. Berrington, N. R. Acute extradural hematoma associated with silastic dural substitute: case report. Surg Neurol. 1992 December; 38(6): 469–70.
11. Brown, P.; Cervenakova, L.; Goldfarb, L. G.; McCombie, W. R.; Rubenstein, R.; Will, R. G.; Pocchiari, M.; Martinez-Lage, J. F.; Scalici, C.; Masullo, C.; et al. Iatrogenic Creutzfeldt-Jakob disease: an example of the interplay between ancient genes and modern medicine. Neurology. 1994 February; 44(2): 291–3.
12. Clavel, M.; Clavel, P. Creutzfeldt-Jakob disease transmitted by dura mater graft. [Review] [10 refs.] Eur Neurol. 1996; 36(4): 239–40.
13. Cohen, A. R.; Aleksic, S.; Ransohoff, J. Inflammatory reaction to synthetic dural substitute. Case report [see comments. Comment in: J. Neurosurg 1989. October; 71(4):629.] J Neurosurg. 1989 April; 70(4): 633–5.
14. Defebvre, L.; Destee, A.; Caron, J.; Ruchoux, M. M.; Wurtz, A.; Remy, J. Creutzfeldt-Jakob disease after an embolization of intercostal arteries with cadaveric dura mater suggesting a systemic transmission of the prion agent. Neurology. 1997 May; 48(5): 1470–1.
15. Esmonde, T.; Lueck, C. J.; Symon, L.; Duchen, L. W.; Will, R. G. Creutzfeldt-Jakob disease and lyophilised dura mater grafts: report of two cases. [Review] [8 refs.] J Neurol Neurosurg Psychiatry. 1993 September; 56(9): 999–1000.
16. Fisher, W. S. 3d; Six, E. G. Cervical myelopathy from dural substitute. Neurosurgery. 1983 December; 13(6): 715–7.
17. Fontana, R.; Talamonti, G.; D'Angelo, V.; Arena, O.; Monte, V.; Collice, M. Spontaneous haematoma as unusual complication of silastic dural substitute. Report of 2 cases. Acta Neurochir. 115(1–2(Wien) 1992): 64–6.
18. Garcia Santos, J. M.; Lopez Corbalan, J. A.; Martinez-Lage, J. F.; Sicilia Guillen, J. CT and MRI in iatrogenic and sporadic Creutzfeldt-Jakob disease: as far as imaging perceives. Neuroradiology. 1996 April; 38(3): 226–31.
19. Gondo, G.; Nakayama, S.; Mochimatsu, Y.; Nakajima, F.; Hasegawa, A. Posterior fossa hemorrhage 11 years after the use of silastic dural substitute: case report]. [Review] [8 refs] [Japanese]. No Shinkei Geka. 1991 January; 19(1): 59–62.
20. Gudmundsson, G.; Sogaard, I. Complications to the use of vicryl-collagen dural substitute. Acta Neurochir. 132 (1–3(Wien) 1995): 145–7.
21. Hainfellner, J. A.; Jellinger, K.; Diringer, H.; Guentchev, M.; Kleinert, R.; Pilz, P.; Maier, H.; Budka, H. Creutzfeldt-Jakob disease in Austria. [German]. Wien Klin Wochenschr. 1996 Dec. 13; 108(23): 759–63.
22. Harvey, I.; Coyle, E. Creutzfeldt-Jakob disease after non-commercial dura mater graft [letter; comment. Comment on: Lancet 1992 Jul., 4.; 340(8810):24–7.] Lancet. 1992 Sep. 5; 340(8819): 615.
23. Johnson, M. H.; Thompson, E. J. Freeze-dried cadaveric dural grafts can stimulate a damaging immune response in the host. Eur Neurol. 1981; 20(6): 445–7.
24. Lane, K. L.; Brown, P.; Howell, D. N.; Crain, B. J.; Hulette, C. M.; Burger, P. C.; DeArmond, S. J. Creutzfeldt-Jakob disease in a pregnant woman with an implanted dura mater graft. Neurosurgery. 1994 April; 34(4): 737–9; discussion 739–40.
25. Martinez-Lage, J. F.; Sola, J.; Poza, M.; Esteban, J. A. Pediatric Creutzfeldt-Jakob disease: probable transmission by a dural graft. [Review] [22 refs.] Childs Nerv Syst. 1993 July; 9(4): 239–42.
26. Marx, R. E.; Carlson, E. R. Creutzfeldt-Jakob disease from allogeneic dura: a review of risks and safety. [Review] [11 refs.] J Oral Maxillofac Surg. 1991 March; 49(3): 272–4; discussion 274–5.
27. Misra, B. K.; Shaw, J. F. Extracerebral hematoma in association with dural substitute. Neurosurgery. 1987 September; 21(3): 399–400.
28. Miyamoto, S.; Kudo, T.; Suzuki, S.; Iwabuchi, T. Formation of postoperative hematoma directly under a silastic dural substitute. [Japanese.] No Shinkei Geka. 1983 September; 11(9): 989–94.
29. Newcombe, R. L. Neurosurgery and iatrogenic transmission of Creutzfeldt-Jakob disease. Med J Aust. 1996 May 20; 164(10): 603–4.
30. Ng, T. H.; Chan, K. H.; Leung, S. Y.; Mann, K. S. An unusual complication of silastic dural substitute: case report. [Review] [12 refs.] Neurosurgery. 1990 September; 27(3): 491–3.
31. Ohbayashi, N.; Inagawa, T.; Katoh, Y.; Kumano, K.; Nagasako, R.; Hada, H. Complication of silastic dural substitute 20 years after dural plasty. [Review] [13 refs.] Surg Neurol. 1994 April; 41(4): 338–41.
32. Ongkiko, C. M. Jr; Keller, J. T.; Mayfield, F. H.; Dunsker, S. B. An unusual complication of Dura Film as a dural substitute. Report of two cases. J Neurosurg. 1984 May; 60(5): 1076–9.
33. Pocchiari, M.; Masullo, C.; Salvatore, M.; Genuardi, M.; Galgani, S. Creutzfeldt-Jakob disease after non-commercial dura mater graft [letter; comment. Comment on: Lancet 1992 Jul., 4.; 340(8810):24–7.] Lancet. 1992 Sep. 5; 340(8819): 614–5.

34. Robertson, S. C.; Menezes, A. H. Hemorrhagic complications in association with silastic dural substitute: pediatric and adult case reports with a review of the literature. [Review] [28 refs.] Neurosurgery. 1997 January; 40(1): 201–5; discussion 205–6.
35. Siccardi, D.; Ventimiglia, A. Fibrotic-haemorrhagic reaction to synthetic dural substitute. Acta Neurochir. 132(1–3(Wien) 1995): 148–9.
36. Simpson, D.; Robson, A. Recurrent subarachnoid bleeding in association with dural substitute. Report of three cases. J Neurosurg. 1984 February; 60(2): 408–9.
37. Spaziante, R.; Cappabianca, P.; Del Basso De Caro, M. L.; de Divitiis, E. Unusual complication with use of lyophylized dural graft. Neurochirurgia. 31(1(Stuttg) 1988 January): 32–4.
38. Taylor, D. M.; McConnell, I. Unconventional transmissible agents in dura mater: significance for iatrogenic Creutzfeldt-Jakob disease [letter.] Neuropathol Appl Neurobiol. 1996 June; 22(3): 259–60.
39. Thadani, V.; Penar, P. L.; Partington, J.; Kalb, R.; Janssen, R.; Schonberger, L. B.; Rabkin, C. S.; Prichard, J. W. Creutzfeldt-Jakob disease probably acquired from a cadaveric dura mater graft. Case report [see comments. Comment in:, J. Neurosurg 1989. December; 71(6):954–5.] J Neurosurg. 1988 November; 69(5): 766–9.
40. Thompson, D.; Taylor, W.; Hayward, R. Haemorrhage associated with silastic dural substitute. [Review] [11 refs.] J Neurol Neurosurg Psychiatry. 1994 May; 57(5): 646–8.
41. Weber, T.; Tumani, H.; Holdorff, B.; Collinge, J.; Palmer, M.; Kretzschmar, H. A.; Felgenhauer, K. Transmission of Creutzfeldt-Jakob disease by handling of dura mater [letter] [see comments. Comment in: Lancet 1993 Mar., 6.; 341(8845):641–2.] Lancet. 1993 Jan. 9; 341(8837): 123–4.
42. Yamada, S.; Aiba, T.; Endo, Y.; Hara, M.; Kitamoto, T.; Tateishi, J. Creutzfeldt-Jakob disease transmitted by a cadaveric dura mater graft. [Review] Neurosurgery. 1994 April; 34(4): 740–3; discussion 743–4.

What is claimed is:

1. A method for promoting meningeal tissue growth to replace a damaged meningeal tissue, said method comprising;

providing certified collagen prepared by a process certified to provide physiologically compatible collagen which is free of effective amounts of active viruses and prions;

forming a cross-linked matrix comprising said certified collagen and pores having a diameter of 10–500 micrometers that permit growing meningeal tissue to infiltrate said matrix, wherein said matrix is substantially free of non-collagenous proteins;

contacting said matrix and said damaged meningeal tissue;

maintaining said contact between said matrix and said damaged meningeal tissue to promote meningeal tissue growth through said matrix; and substantially resorbing said matrix.

2. The method of claim 1, wherein said matrix is a planar object and conforms on contact to a surface contour of an organ underlying said damaged meningeal tissue.

3. The method of claim 1, wherein said pores have an average diameter of about 50 to about 150 microns.

4. The method of claim 1, wherein said pores proximate to a surface of said matrix are outermost pores ranging in diameter from about 30 μm to about 150 μm and a balance of said pores are innermost pores ranging in diameter from about 50 μm to about 300 μm.

5. The method of claim 4, wherein said outermost pores are about 70 μm in diameter and said innermost pores are about 150 μm in diameter.

6. The method of claim 1, wherein said matrix is a sponge.

7. The method of claim 1, wherein said matrix is a film.

8. The method of claim 1, wherein said matrix is a non-woven or a felt.

9. The method of claim 1, wherein said collagen is derived from a bovine source.

10. The method of claim 9, wherein said collagen is derived from bovine corium.

11. The method of claim 9, wherein said collagen is derived from bovine tendon.

12. The method of claim 1, wherein said certified process comprises alkalinizing said material to a pH of about 13 to about 14 to substantially remove contaminating glycoproteins and lipids.

13. The method of claim 1, wherein said collagen is obtained by a process comprising:

cleaning extraneous matter from a native source of Type I collagen;

washing said cleaned collagen containing material;

comminuting said washed collagen containing material;

digesting said comminuted collagen containing material with a proteolytic enzyme to substantially remove elastin and non-collagenous impurities which can cause antigenic activity and to swell said collagen;

inactivating said proteolytic enzyme;

washing said enzymatically digested collagen containing material to substantially remove excess enzyme and non-collagenous protein impurities;

alkalinizing said collagen containing material to a pH of about 13 to about 14, at a temperature of about 25° C. to about 30° C. for a period of about 35 to about 48 hours, to substantially remove contaminating glycoproteins and lipids;

neutralizing said alkalinized collagen containing material with an acid;

washing said neutralized collagen containing material;

acidifying said washed and neutralized collagen containing material to a pH of about 2 to about 3 to further swell said material, wherein said acidifying does not employ an acid that causes substantial cross-linking of collagen;

homogenizing said acidified collagen containing material;

filtering said homogenized collagen containing material to remove unswollen, non-collagenous material from collagen fibers; and collecting said filtered collagen fibers for use in said matrix.

14. The method of claim 13, wherein said proteolytic enzyme is ficin or pepsin.

15. The method of claim 13, wherein said digesting step comprises adding about one part of proteolytic enzyme per 150 parts of said collagen containing material, adjusting a pH of said collagen containing material to about 6.0 to about 6.3, and digesting said collagen containing material for about 1 to about 2 hours at a temperature of about 36.5° C. to about 37.5° C.

16. The method of claim 15, wherein said proteolytic enzyme is ficin.

17. The method of claim 13, wherein said enzyme is inactivated by adding an oxidizing agent to said enzymatically digested collagen containing material.

18. The method of claim 17, wherein said oxidizing agent is sodium chlorite.

19. The method of claim 13, wherein said method further comprises further washing with dilute aqueous hydrogen peroxide said washed and enzyme inactivated collagen containing material.

20. The method of claim 13, wherein said alkalinizing employs an aqueous solution of about 5% sodium hydroxide and about 20% sodium sulfate.

21. The method of claim 13, wherein said acidifying step employs acetic acid, hydrochloric acid or lactic acid to adjust said pH.

22. The method of claim 13, wherein said acidifying step employs aqueous lactic acid to adjust said pH, and said method further comprises:

forming an aqueous dispersion of said filtered collagen fibers;

precipitating collagen fibers from said aqueous dispersion by addition of ammonium hydroxide; and casting a dispersion of said precipitated collagen fibers to form said matrix.

23. The method of claim 1, wherein said collagen is non-antigenic.

24. The method of claim 1, wherein said matrix connects undamaged portions of meningeal tissue adjacent to said damaged meningeal tissue.

25. The method of claim 1, wherein said damaged meningeal tissue is a human spinal dura.

26. The method of claim 1, wherein said damaged meningeal tissue is a human cerebral dura.

27. The method of claim 1, wherein said damaged meningeal tissue contacted with said matrix defines a margin of presumptively benign tissue surrounding a surgically excised section of cancerous tissue.

28. The method of claim 1, wherein said matrix is sutured to said damaged meningeal tissue.

29. The method of claim 1, wherein said matrix is not sutured to meningeal tissue.

30. The method of claim 1, wherein said matrix is not mechanically or chemically bonded to meningeal tissue by artificial means.

31. The method of claim 1, wherein said matrix further comprises an effective amount of a meningeal tissue growth factor.

32. The method of claim 31, wherein said meningeal tissue growth factor is selected from the group consisting of RGD containing peptides, decorin, laminin, merosin, chondroitin sulfate, dermatin sulfate, heparan sulfate, keratin sulfate, basic fibroblast growth factor, fibronectin, entactin and tenascin.

33. The method of claim 31, wherein said pores have an average diameter of about 50 to about 150 microns.

34. The meningeal tissue growth matrix of claim 31, wherein said pores proximate to a surface of said matrix are outermost pores ranging in diameter from about 30 $\mu$m to about 150 $\mu$m and a balance of said pores are innermost pores ranging in diameter from about 50 $\mu$m to about 300 $\mu$m.

35. The method of claim 34, wherein said outermost pores are about 70 $\mu$m in diameter and said innermost pores are about 150 $\mu$m in diameter.

36. The method of claim 31, wherein said certified process comprises:

cleaning extraneous matter from a native source of Type I collagen;

washing said cleaned collagen containing material;

comminuting said washed collagen containing material;

digesting said comminuted collagen containing material with a proteolytic enzyme to substantially remove elastin and non-collagenous impurities which can cause antigenic activity and to swell said collagen;

inactivating said proteolytic enzyme;

washing said enzymatically digested collagen containing material to substantially remove excess enzyme and non-collagenous protein impurities;

alkalinizing said collagen containing material to a pH of about 13 to about 14, at a temperature of about 25° C. to about 30° C. for a period of about 35 to about 48 hours, to substantially remove contaminating glycoproteins and lipids;

neutralizing said alkalinized collagen containing material with an acid;

washing said neutralized collagen containing material;

acidifying said washed and neutralized collagen containing material to a pH of about 2 to about 3 to further swell said material, wherein said acidifying does not employ an acid that causes substantial cross-linking of collagen;

homogenizing said acidified collagen containing material;

filtering said homogenized collagen containing material to remove unswollen, non-collagenous material from collagen fibers; and collecting said filtered collagen fibers for use in said matrix.

37. The method of claim 36, wherein said acidifying step employs aqueous lactic acid to adjust said pH, and said process further comprises:

forming an aqueous dispersion of said filtered collagen fibers;

precipitating collagen fibers from said aqueous dispersion by addition of ammonium hydroxide; and casting a dispersion of said precipitated collagen fibers to form said matrix.

38. The method of claim 36, wherein said matrix is a sponge, a film, a non-woven or a felt.

39. The method of claim 36, wherein said collagen is derived from a bovine source.

40. The method of claim 39, wherein said collagen is derived from bovine corium or tendon.

41. The method of claim 36, wherein said collagen is human collagen expressed by a transgenic animal which is not a human.

42. The method of claim 31, wherein said meningeal tissue growth factor is a ligand for integrin.

43. The method of claim 1, wherein said matrix forming comprises:

forming said certified collagen into at least two different members selected from the group consisting of a film, a sponge, a non-woven and a felt; and bonding said at least two different members together to provide said matrix.

44. The method of claim 43, wherein said at least two different members are a film and a sponge.

45. The method claim 43, wherein said at least two different members are a sponge and two sheets of film, and said sponge is laminated between said two sheets of film.

46. The method of claim 43, wherein said matrix further comprises an effective amount of a meningeal tissue growth factor.

47. The method of claim 46, wherein said meningeal tissue growth factor is selected from the group consisting of RGD containing peptides, decorin, laminin, merosin, chondroitin sulfate, dermatin sulfate, heparan sulfate, keratin sulfate, basic fibroblast growth factor (bFGF), fibronectin entactin and tenascin.

48. The method of claim 46, wherein said meningeal tissue growth factor is a ligand for integrin.

49. The method of claim 43, wherein at least one porous-member of said at least two different members has pores of a sufficient size and quantity to permit growing meningeal tissue to infiltrate therein, and at least one suturable member of said at least two different members is sufficiently durable to hold a suture.

50. The method of claim 49, wherein said pores have an average diameter of about 50 to about 150 microns.

51. The method of claim 49, wherein said pores proximate to a surface of said porous member are outermost pores ranging in diameter from about 30 µm to about 150 µm and a balance of said pores are innermost pores ranging in diameter from about 50 µm to about 300 µm.

52. The method of claim 51, wherein said outermost pores are about 70 µm in diameter and said innermost pores are about 150 µm in diameter.

53. The method of claim 43, wherein said matrix is planar.

54. The method of claim 43, wherein said certified process comprises:
cleaning extraneous matter from a native source of Type I collagen;
washing said cleaned collagen containing material;
comminuting said washed collagen containing material;
digesting said comminuted collagen containing material with a proteolytic enzyme to substantially remove elastin and non-collagenous impurities which can cause antigenic activity and to swell said collagen;
inactivating said proteolytic enzyme;
washing said enzymatically digested collagen containing material to substantially remove excess enzyme and non-collagenous protein impurities;
alkalinizing said collagen containing material to a pH of about 13 to about 14, at a temperature of about 25° C. to about 30° C. for a period of about 35 to about 48 hours, to substantially remove contaminating glycoproteins and lipids;
neutralizing said alkalinized collagen containing material with an acid;
washing said neutralized collagen containing material;
acidifying said washed and neutralized collagen containing material to a pH of about 2 to about 3 to further swell said material, wherein said acidifying does not employ an acid that causes substantial cross-linking of collagen;
homogenizing said acidified collagen containing material;
filtering said homogenized collagen containing material to remove unswollen, non-collagenous material from collagen fibers; and
collecting said filtered collagen fibers for use in said matrix.

55. The method of claim 54, wherein said acidifying step employs aqueous lactic acid to adjust said pH, and said process further comprises:
forming an aqueous dispersion of said filtered collagen fibers;
precipitating collagen fibers from said aqueous dispersion by addition of ammonium hydroxide; and
casting a dispersion of said precipitated collagen fibers to form said matrix.

56. The method of claim 43, wherein said collagen is derived from a bovine source.

57. The method of claim 56, wherein said collagen is derived from bovine corium or tendons.

58. The method of claim 43, wherein said collagen is human collagen expressed by a transgenic animal which is not a human.

59. The method of claim 43, wherein said matrix forming further comprises:
providing at least two different volumes of a liquid medium containing said certified collagen; and
evaporating said liquid medium from each of said different volumes to provide said at least two different members of the group consisting of a film, a sponge, a non-woven and a felt.

60. The method of claim 1, wherein said matrix forming further comprises:
providing a volume of a liquid medium containing said certified collagen; and
evaporating said liquid medium to provide said matrix.

61. The method of claim 1, wherein said matrix is provided with a plurality of layers, including a high porosity layer and a low porosity layer, said high porosity layer being more porous than said low porosity layer.

62. The method of claim 61, wherein said high porosity layer is a collagen sponge and said low porosity layer is a substantially water-impermeable, suturable film bonded to said collagen sponge.

63. The method of claim 1, wherein said matrix is substantially resorbed within about three months after implantation.

64. The method of claim 1, wherein said matrix has a density of about 0.0001 mg/mm$^3$ to about 0.12 mg/mm$^3$.

65. The method of claim 1, wherein said matrix has a density of about 0.009 mg/mm$^3$.

66. The method of claim 1, wherein said matrix is not continuously sutured about its perimeter to meningeal tissue.

67. A method for promoting meningeal tissue growth to replace a damaged meningeal tissue, said method comprising:
providing certified collagen prepared by a process certified to provide physiologically compatible collagen which is free of effective amounts of active viruses and prions;
forming a cross-linked matrix consisting essentially of said certified collagen and optionally, at least one meningeal tissue growth factor, wherein said matrix has pores having a diameter of 10–500 micrometers that permit growing meningeal tissue to infiltrate said matrix;
contacting said matrix and said damaged meningeal tissue;
maintaining said contact between said matrix and said damaged meningeal tissue to promote meningeal tissue growth through said matrix; and
substantially resorbing said matrix.

68. The method of claim 67, wherein said matrix consists essentially of said certified collagen and said at least one meningeal tissue growth factor.

69. A matrix for promoting meningeal tissue growth to replace a damaged meningeal tissue, said matrix prepared by a process comprising:
providing certified collagen fibers which are physiologically compatible and certified to be free of effective amounts of active viruses and prions;

dispersing said certified collagen fibers in a liquid medium to provide a collagen dispersion; and evaporating said liquid medium from said collagen dispersion to provide said matrix;

wherein said matrix comprises said certified collagen fibers and pores having a diameter of 50–150 micrometers adapted to permit growing meningeal tissue to infiltrate said pores, said matrix is substantially free of non-collagenous proteins, and said matrix is adapted to be resorbed within about three months after implantation.

70. The matrix of claim 69, wherein said matrix is a planar object adapted to conform on contact to a surface contour of an organ underlying said damaged meningeal tissue being replaced.

71. The matrix of claim 69, wherein said pores have an average diameter of about 50 to about 150 $\mu$m.

72. The matrix of claim 69, wherein said pores proximate to a surface of said matrix are outermost pores ranging in diameter from about 50 $\mu$m to less than about 150 $\mu$m and a balance of said pores are innermost pores having a larger diameter than said outermost pores.

73. The matrix of claim 69, wherein said pores proximate to a surface of said matrix are outermost pores having an average diameter of about 70 $\mu$m and a balance of said pores are innermost pores having an average diameter of about 150 $\mu$m.

74. The matrix of claim 69, wherein said matrix is a sponge.

75. The matrix of claim 69, wherein said matrix is a film.

76. The matrix of claim 69, wherein said matrix is a non-woven or a felt.

77. The matrix of claim 69, wherein said matrix is adapted to provide a liquid-tight seal against cerebrospinal fluid leakage without mechanical or chemical bonding to meningeal tissue.

78. A matrix for promoting meningeal tissue growth to replace a damaged meningeal tissue, said matrix prepared by a process comprising:

providing certified collagen fibers which are physiologically compatible and certified to be free of effective amounts of active viruses and prions;

providing at least two different volumes of a liquid medium containing said certified collagen; and evaporating said liquid medium from each of said different volumes to provide at least two different members of the group consisting of a film, a sponge, a non-woven and a felt, and wherein said matrix comprises said at least two different members, said certified collagen fibers, and pores having a diameter of 50–150 $\mu$m adapted to permit growing meningeal tissue to infiltrate said pores, and wherein said matrix is substantially free of non-collagenous proteins, and said matrix is adapted to be resorbed within about three months after implantation.

* * * * *